United States Patent
Fregonese (12)

(10) Patent No.: US 6,270,811 B1
(45) Date of Patent: Aug. 7, 2001

(54) PHARMACEUTICAL, COSMETIC COMPOSITION WITH BASE OF MICROBIAL CULTURE MIXED WITH AN ESSENTIAL OIL AND AN ACID

(75) Inventor: Alexandra Fregonese, Laplume (FR)

(73) Assignee: 1 Fois 1 Jour Concept, Laplume (FR)

( * ) Notice: Subject to any disclaimer, the term of this patent is extended or adjusted under 35 U.S.C. 154(b) by 0 days.

(21) Appl. No.: 09/308,250

(22) PCT Filed: Nov. 26, 1997

(86) PCT No.: PCT/FR97/02127

§ 371 Date: May 25, 1999

§ 102(e) Date: May 25, 1999

(87) PCT Pub. No.: WO98/23243

PCT Pub. Date: Jun. 4, 1998

(30) Foreign Application Priority Data

Nov. 26, 1996 (FR) .................................................. 96 14442

(51) Int. Cl.[7] .............................. A61K 35/00; A61K 6/00; A61K 7/00
(52) U.S. Cl. .................... 424/780; 424/725; 424/736; 424/747; 424/115; 424/401; 514/886; 514/887
(58) Field of Search ................................ 424/195.1, 93.4, 424/93.51, 115, 401, 780, 747, 736, 725; 514/886, 887

(56) References Cited

U.S. PATENT DOCUMENTS 4,464,362 * 8/1984 Kludas et al. ..................... 424/195.1
5,019,391 * 5/1991 Bunte et al. ....................... 424/195.1

FOREIGN PATENT DOCUMENTS

0043128 * 1/1982 (EP) .
0297457 * 1/1989 (EP) .
2222088 * 10/1974 (FR) .
2573651 * 5/1996 (FR) .

OTHER PUBLICATIONS

Lawless, J. Illustr. Encyclop. of Essential Oils, Element Books Ltd. —Publ., Gr. Britian, pp. 56–61, 1995.*
Tanno et al. Chem. Abstracts. vol. 125, No. 22, abstract No. 284382, Nov. 1996.*
Sasaki et al. Chem. Abstracts. vol. 127, No. 14, see abstract, Oct. 1997.*

* cited by examiner

*Primary Examiner*—Christopher R. Tate
(74) *Attorney, Agent, or Firm*—Dennison, Scheiner, Schultz & Wakeman

(57) ABSTRACT

The invention concerns a cosmetic or pharmaceutical composition. This composition is characterised in that it contains a microbial culture compatible in cosmetics or in pharmacy or in therapy, in particular a culture of micro-organisms selected among the acetic or lactic bacteria, freeze-dried yeast, suspensions of micro-organisms, fermented organic substances, for example fermented pollen, or an inactivated culture of bacteria of the genus bifidobacterium or of bacteria related to this genus mixed with an essential oil and an acid preferably an organic acid, such as citric acid. This composition has an activity for regenerating the skin, in particular anti-wrinkle properties, for erasing old scars, for repairing burnt tissues, for promoting skin healing, for eliminating pigmentary spots and also for promoting growth or fresh growth of superficial body growth including nails, hair or hairs.

41 Claims, No Drawings

PHARMACEUTICAL, COSMETIC COMPOSITION WITH BASE OF MICROBIAL CULTURE MIXED WITH AN ESSENTIAL OIL AND AN ACID

BACKGROUND OF THE INVENTION

It is known from the EP-0 043 128 B1 corresponding to U.S. Pat. No. 4,464,362 document of a cosmetic composition based on a "complex" of active substances which promote the process of repair of DNA of the cells of the skin based on an inactivated culture of bacteria of the genus Bifidobacterium or of bacteria related to this genus (see claim 1 and the description).

This document describes a DNA repairing effect which is demonstrated by comparative tests wherein tissue DNA is damaged in vitro or in vivo by a UV lamp and wherein it is demonstrated that the complex of active substances formed by inactivated cultures of Bifidobacterium produces a significant repairing effect.

This document also contains various examples of embodiments in which this complex is used in combination with various mixtures of esters of high molecular weight some of which can be alcoholic esters of citric acid.

SUMMARY OF THE INVENTION

Within the context of the present invention, tests have been made on wrinkles as well as on several years old-scars which can be up to about twenty years old, with a composition in accordance with the examples in this document and no significant anti-wrinkle effect nor any apparent effects on the appearance of such old scars was noted.

The present inventor has, in new tests, prepared a mixture of an inactivated culture of Bifidobacterium or of bacteria related to this genus with an essential oil as well as an acid, preferably an organic acid, in particular a fatty acid, such as citric acid, and has demonstrated the unexpected obtaining of a significant anti-wrinkle effect as well as a significant effect of erasing old scars. These significant effects are quantifiable as from the first application. It has also been possible to observe a significant effect in relation to the repair of scars left by buns, promoting skin healing, removing pigment marks and also promoting the growth or the re-growth of the integuments, i.e. the nails, the hair or the hairs.

The present inventor, during even more tests, has unexpectedly discovered that the use of pollen from flowers, which contains a significant number of fermentation micro-organisms or ferments, or of its aqueous or organic extracts, in particular lipidic extracts, which is collected or not by bees, and which is non-fermented or fermented, constitutes an active principle of a cosmetic or pharmaceutical composition, in particular having an anti-wrinkle, smoothening, skin texture improving, lightening, scar diminishing, skin surface moisturising, skin softening, perfuming, skin regenerating effect. It has also been possible to unexpectedly observe that this activity was radically reinforced if the pollen was combined with a plant essential oil, in particular with an essential oil of mint, preferably peppermint, of rosemary, of lemon and more if this combination was also prepared with an acid, preferably an organic acid, in particular a fatty acid. Advantageously, the acid mentioned above is selected from citric acid used as such or in the form of a derivative such as a salt or ester and especially an alcoholic ester, or a citrus fruit juice such as lemon juice, orange juice, lime juice, grapefruit juice, clementine juice, mandarin juice, or an essential oil of lemon or of orange or of other extracts which are rich in citric acid or tartaric acid, or ascorbic acid or lactic acid.

More generally, the present inventor has discovered that a microbial culture compatible in cosmetics or in pharmacy, in particular a culture of micro-organisms selected from acetic or lactic bacteria, lyophilised yeasts, suspensions of micro organisms, fermented organic materials, for example pollen, preferably fermented pollen, or an inactivated culture of bacteria of the genus Bifidobacterium or of bacteria related to this genus, constitutes an active principle of a cosmetic or pharmaceutical composition, having the activities mentioned above which are particularly powerful in a mixture with an essential oil and an acid.

DESCRIPTION OF THE INVENTION

Thus, according to a first aspect, the present invention relates to the use of a microbial culture compatible in cosmetics or in pharmacy, in particular a culture of micro-organisms selected from acetic or lactic bacteria, lyophilised yeasts, suspensions of micro-organisms, fermented organic materials, for example pollen, preferably fermented pollen, or an inactivated culture of bacteria of the genus Bifidobacterium or of bacteria related to this genus in a mixture with an essential oil and an acid, preferably an organic acid, in particular a fatty acid, as cosmetic agent, or for preparing a pharmaceutical composition especially having an activity for regenerating the skin, particularly an anti-wrinkle activity, for erasing old scars, for repairing scars left by burns, for promoting skin healing, for removing pigment marks and also for promoting growth or re-growth of integuments, comprising nails and hair or hairs.

It is to be noted that these effects are obtained without notable side effect and especially without comedogenic effect and without allergenic effect and without hyperaemia. It is to be noted that in order to guarantee an absence of hyperaemia, it is in general necessary to use an amount of acid, preferably an organic acid, in particular a fatty acid, such as citric acid, of less than or equal to about 30%.

According to a second aspect, the present invention also covers a cosmetic or pharmaceutical composition, characterised in that it comprises a microbial culture compatible in cosmetics or in pharmacy, in particular a culture of micro-organisms selected from acetic or lactic bacteria, lyophilised yeasts, suspensions of micro-organisms, fermented organic materials, for example pollen, preferably fermented pollen, or an inactivated culture of bacteria of the genus Bifidobacterium or of bacteria related to this genus, in a mixture with an essential oil and an acid, preferably an organic acid, in particular a fatty acid.

According to an advantageous embodiment of the invention, and in the context of any one of its aspects, the microbial culture mentioned above is used at a concentration of micro-organisms of at least 1 million, preferably of at least 10 million per gram of culture of micro-organisms. "Culture" is understood as meaning the crude culture media or those resulting from a physical separation such as a filtration, centrifugation, which are well known to the person skilled in the art and which are also described further on in relation to the pollen.

It is possible for this microbial culture to be constituted of about 1 to about 90% by weight of the final composition but in general it will be possible to vary, within preferred concentrations as indicated according to the variants below.

According to an embodiment variant of the invention, about 1 to about 90% by weight and preferably about 50 to about 60% by weight of an inactivated culture of bacteria of the genus Bifidobacterium or of bacteria related to this genus can be incorporated.

According to another implementation variant of the invention, when fermented organic materials are involved, for example non-fermented or fermented pollen, it is currently preferred to incorporate about 1 to about 90% by weight, preferably about 1 to about 30%, more preferably about 1 to about 10% and more preferably between about 1 and about 5% of such fermented organic materials, preferably constituted of fermented pollen.

As regards the acid, this will generally be added at a proportion of about 1 to about 50% by weight and preferably about 5 to about 40% by weight and more preferably between about 5 and about 30% by weight.

In either of the aspects of the present invention, it is currently preferred to use as acid citric acid as such or in the form of a derivative such as a salt or ester and especially an alcoholic ester, or a citrus fruit juice, such as lemon juice, orange juice, lime juice, grapefruit juice, clementine juice, mandarin juice, or an essential oil of lemon or of orange or of other extracts which are rich in citric acid or an tartaric acid, or ascorbic acid or lactic acid. The acid can also be a fatty acid compatible in cosmetics or in pharmacy, well known to the person skilled in the art. It has appeared that the presence of this acid improves the effect in a synergistic manner, within the context of all the activities observed.

Similarly, it is currently preferred to apply about 0.5 to about 10% by weight of essential oil and more preferably about 1 to about 7% by weight. This essential oil is at least one plant essential oil selected from the group consisting of an essential oil of mint, of an essential oil of rosemary, an essential oil of thyme and an essential oil of wild thyme, or any one of a mixture thereof. Preferably, this essential oil is an essential oil of mint.

It has also revealed to be advantageous to further incorporate another essential oil, and in particular an essential oil of rosemary.

In the case of application of mixtures of essential oils, it is currently preferred to also apply the same total concentration of essential oils. However, the total content of essential oil will vary preferably between about 0.5 and about 10% by weight and more preferably between about 1 and about 7% by weight.

Naturally, other products which are usually present in cosmetic or pharmaceutical products can be added without harming the effect of such combinations, or preferably for improving in contrast the effect of such a combination. In this context, proteins can also be added, especially structural proteins such as collagen or elastin, especially their soluble forms and also the hydrolysates of such proteins. The addition of these proteins enables increasing the resistance of the skin to the treatment.

It is also possible to consider excipients which are usually used in cosmetics or pharmacy, and especially for a topical application or a sub-cutaneous application.

On the other hand, within the context of the use by the public, it is highly preferred to incorporate the mixture mentioned above according to the invention of the microbial culture with an essential oil as well as an acid, alone, or in a mixture with other additional ingredients set forth above, in a total proportion which is not greater than about 30% by weight, the remainder, i.e. about 70%, being constituted of other texture agents which can be simply constituted by cosmetic products which are available on the market to which the mixture(s) according to the invention are added in this maximum proportion of about 30%. These other cosmetic products can be cosmetic products for erasing, creams, masks, sera, whether they be used for the skin or the hair, and this enables decreasing, even preventing any phenomenon of irritation which is not acceptable within the context of a product for the public.

According to a third aspect, the present invention further covers a method of cosmetic, pharmaceutical or therapeutic treatment, characterised in that it comprises the administration to a mammal, in particular a human being or an animal, of an effective amount of a microbial culture compatible in cosmetics or pharmacy or therapy, in particular a culture of micro-organisms selected from acetic or lactic bacteria, lyophilised yeasts, suspensions of micro-organisms, fermented organic materials, for example pollen, preferably fermented pollen, or an inactivated culture of bacteria of the genus Bifidobacterium or of bacteria related to this genus in a mixture with an essential oil, and of an acid, preferably an organic acid, in particular a fatty acid. Advantageous characteristics of this method also emerge clearly from the advantageous characteristics described above, especially in relation to the employment as acid of citric acid, to the optional incorporation of another essential oil in particular an essential oil of rosemary, with the indicated proportions.

According to a preferred embodiment of the method of treatment, prior to the application of the mixture mentioned above or of a composition containing same, as defined above, a moisturising agent, for example a serum, is applied. It is possible to use, as moisturising agent, a concentrated complex of active agents which bring about all the essential biological elements to the epidermis. It can be a composition which contains, for example, an extract of algae, of aloe vera, of hyaluronic acid, an extract of Thymus, of hydroforte, taken alone or as a mixture.

According to a fourth aspect, the present invention also covers the use of pollen from flowers, or of its aqueous or organic extracts, particularly lipidic extracts, as cosmetic agent or for preparing a pharmaceutical composition, especially having a skin regenerating activity, particularly an anti-wrinkle activity, old scars erasing activity, an activity for repairing scars left by burns, an activity for promoting skin healing, an activity for removing pigment marks, an activity permitting a lightening of the skin, skin surface moisturising, skin softening, perfuming activity.

Naturally, the pollen from flowers or aqueous or organic extracts, particularly lipidic extracts, can be used according to the present invention also for the implementation of any one of the other aspects of the invention mentioned above.

The use of pollen from flowers or of its aqueous or organic extracts, particularly lipidic extracts, constitutes an invention which is patentable independently of the other aspects of the invention.

For any one of the aspects of the invention, it is possible to use the pollen from flowers, or of its aqueous or organic extracts, particularly lipidic extracts, in the state in which it is collected by bees, or collected independently, also in the non-fermented or fermented state, natural or enriched with lactic ferments for example from bacteria and/or from yeasts, in particular yeasts which can be isolated from pollen or from bees.

The pollen from flowers of the invention can itself be used in a lyophilised state or even having been concentrated by a physical method such as centrifugation or filtration for example.

Within the context of the invention, the organic extract is advantageously an alcoholic extract or aqueous alcohol extract with a $C_1$–$C_6$ lower alcohol, in particular with ethanol, in the case of a water/alcohol mixture, the alcohol concentration is generally 40 to 60% by weight.

On the other hand, according to an advantageous characteristic of the invention, it is preferred to carry out a fermentation of the pollen from flowers or of its aqueous or organic extracts, particularly lipidic extracts, by adding more than 5% of water, and preferably between 20 and 40% by weight of water, or of a nutrient broth containing proteins, enriched or not with a microbial ferment to fresh or frozen pollen which can then be incubated for half a day to several days at an appropriate temperature, generally between 10° C. and about 50° C.

According to an advantageous characteristic of the invention, this fermentation of the pollen can be followed by a soaking with at least one essential oil and/or in the presence of an acid, preferably an organic acid, in particular a fatty acid, preferably for a few hours and advantageously between about 1 h and about 6 h, at a non-critical temperature which can be ambient temperature, generally between about 0° C. and 50° C. It is to be noted that this soaking enables stopping the prior fermentation process.

As essential oils, it is possible to use any essential oil of plants, and it is currently preferred an essential oil of mint, in particular of peppermint, of rosemary, of lemon, as well as mixtures thereof.

It is also possible to mix the pollen with a vegetable oil such as a first cold pressing vegetable oil, such as sunflower oil or soya oil or an oil extracted from pollen for example by an organic solvent, by pressure or by supercritical $CO_2$.

It is also possible to mix the pollen with agents which procure a texture, known as texture agents, such as propylene glycol, poly(vinyl alcohol), glycerol, polyvinylpyrrolidone, a gellifying agent such as xanthane, pectin, an alginate, gum agar, without limitation, for example carbopol.

It is also possible to consider completing this mixture with a little 95° alcohol, or with alcoholic liquor having an alcoholic degree of at least 20°.

It is also possible to complete the pollen with beeswax and/or propolis and/or with honey.

According to a fifth aspect, the present invention also covers a cosmetic or pharmaceutical composition, characterised in that it comprises as active principle pollen from flowers, preferably a fermented pollen or of its aqueous or organic extracts, particularly lipidic extracts, as defined above, alone or in combination with the other active ingredients set forth above.

According to a sixth aspect, the present invention also covers a method of cosmetic, pharmaceutical or therapeutic treatment, characterised in that it comprises the administration to a mammal, in particular a human being or an animal, of an effective amount of a pollen from flowers, preferably a fermented pollen, or of its aqueous or organic extracts, particularly lipidic extracts, for the cosmetic, pharmaceutical or therapeutic effect sought after. Advantageous characteristics of this method also emerge clearly from the advantageous characteristics described above, especially in relation to the use of an acid and/or to the optional incorporation of an essential oil with the proportions indicated.

As regards the pollen, this can be fresh, coming from the hive, or placed to freeze for a few hours to several days after the bees have collected it. Then, it can be lyophilised or dried or packaged under vacuum or under a protective atmosphere such as nitrogen, carbon dioxide and/or oxygen. This pollen can also be autoclaved at 120° C. for 15 minutes in solution in water or an aqueous solution.

As regards the nutrient broth used for the fermentation, this can be distilled water which is sterile or not. This can be non-sterilised water containing organic materials or even a solution enriched with micro-organisms at a content greater than several million per gram of water.

These micro-organisms such a yeasts, lactic flora, such as the genus bifidus or lactobacillus or streptococcus, can originate from isolation from fresh pollen or can come from other sources.

For the fermentation, the fermentation broth is added to the pollen at a concentration of greater than 5% by weight, in practice, generally an average concentration of between 20 and 40% by weight. This bath can be left soaked at a temperature of between +10 and +50° C., optimally between about 25° C., i.e. ambient temperature, at about 35° C., for a period of time of 1 h to 5 days, and generally 1 to 2 days.

At this stage after fermentation, it is possible to use centrifugation-filtration techniques to recover the pollen or to concentrate the new solution of micro-organisms.

As said before, the techniques of physical concentrations such as centrifugation, filtration, can be used to obtain contents of micro-organisms of greater than 1 million per gram, preferably of at least 10 million per gram and even attain 1 billion per gram of pollen or of culture or of "broth". This broth can contain autoclaved pollen or pollen which has been treated by high pressure, for example a pascalisation at more than 3,000 bar for more than 60 min. An ionisation treatment can also be carried out.

It is also possible to stabilise the non-fermented, or preferably fermented pollen, by using various stabilisation techniques, in particular a treatment at high pressures and/or an addition of acid substances, which are advantageously authorised in cosmetics or in pharmacy, such as citric acid or lemon juice, an essential oil of a citrus fruit such as lemon, orange, grapefruit.

The whole of the components of the invention can also be mixed with other cosmetically or pharmaceutically acceptable excipients, as is understandable to the person skilled in the art.

Other aims, characteristics and advantages of the invention will emerge clearly in the light of the explanatory description which will be made with reference to several examples of compositions as well as various tests which have been carried out. In the Examples, all the percentages are given by weight and the temperature is ambient temperature and the pressure is atmospheric, unless otherwise indicated.

EXAMPLE 1

Basic Composition According to the Invention

A basic composition is prepared which comprises the following active ingredients:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 90 g |
| b) Commercial essential oil of mint, for example mentha piperata | about 5 g |
| c) Citric acid | about 5 g |

In order to prepare this composition, the citric acid is firstly mixed with the essential oil of mint, and the complex of inactivated cultures of bacteria is then incorporated, and is mixed up to homogeneity.

This composition can be used as such for constituting a cosmetic or pharmaceutical composition for obtaining the effects described above according to the invention and which are also demonstrated by the tests given below.

This composition can be applied once only, topically on the areas concerned of the skin of a mammal, preferably a human being.

In this context, the following effects were observed:

a) On Wrinkles and Small Wrinkles

A single application of the composition above with a massage for about ten minutes enables observing a complete penetration of the composition, it was possible to observe that the wrinkles and small wrinkles are shallower, shorter.

On the other hand, with a daily application for one or two weeks, it is observed that the wrinkles and small wrinkles are progressively erased.

b) Tissue Loosening

As from the first application of the composition above, a very clear improvement is noted of the contour and of the oval of the face.

c) Crumpled Appearance due to Drying Out

As from the first application of the composition above, a spectacular result is noted: the skin becoming clearly smoother and firmer.

d) the Shadows Under the Eyes

As from the first application of the composition above, it is observed that the shadows under the eyes have a different relief which entirely modifies the look and gives the face a clearly younger and more relaxed appearance.

e) Pouches

An immediate result is noted as from the first application with a tensor effect which decreases the puffiness and enables obtaining a firmness appearance which changes the whole look expression and by that, even the face.

f) Treatment of Scars

Tests of treatment of old scars were also carried out.

In this context, the length and the breadth of the scar concerned was initially measured. Scars as old as thirty years old were treated.

A modification of the shape and the appearance of the scar was observed as from the first application of a composition above, the length and the breadth of which scar, therefore the surface, decreases. A repeated application over several days will lead to an almost complete disappearance of this scar. The invention therefore enables obtaining an effect of erasing the old scars.

g) Repair of Burnt Tissues

In order to treat burnt tissues, it is preferred to use a citric acid content which is not greater than about 3% by weight.

A composition according to the invention above can therefore be applied which is modified to have a citric acid content which is not greater than about 3%, it being possible for the remainder to be constituted by a texture agent in order to obtain a cream which will be applied in a thick layer onto the tissues burnt by rubbing or by an intense heat. A visual improvement of these tissues is observed as from the first application and after several applications, the appearance of a skin having a surface which is essentially similar to the neighbouring areas of skin which have not been subjected to burns. The composition of Example 8 below can also be applied.

h) Removal of Pigment Marks

A significant decrease in the intensity of the pigment mark is observed as from the first application by application of the composition above onto the pigment marks, and after a daily application for several days, a progressive disappearance of the pigment mark is observed, and this is remarkable.

This mixture does not cause any hyperaemia and lightens the tint.

i) Promotion of the Growth or the Re-growth of the Integuments Comprising Nails Hair or Hairs A significant effect of promoting growth or re-growth of integuments is observed with application of the composition above, after a daily application for about two weeks.

Furthermore, the whole of these effects is obtained without any notable side effect, notably without any comedogenic effect on the skin which is an additional advantage for greasy skins which up to now were subject to comedones after the application of anti-wrinkle products which exist on the market which were too rich in fatty substances.

EXAMPLE 2

Composition According to the Invention

A basic composition comprising the following active ingredients is prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 63 g |
| b) Commercial essential oil of mint, for example mentha piperata | about 7 g |
| c) Citric acid | about 30 g |

In order to prepare this composition, the citric acid is firstly mixed with the essential oil of mint, and the complex of inactivated cultures of bacteria is then incorporated and is mixed up to homogeneity.

As a composition, it can be used as such for constituting a cosmetic or pharmaceutical composition for obtaining the effects described above according to the invention and which have also been demonstrated by tests of the type of those set forth in Example 1.

A much more marked effect is obtained for each one of the activities above, which constitutes a synergistic effect and which is due to a proportion of acids in the preferred advantageous range of 5 to 30% by weight.

EXAMPLE 3

More Complete Composition According to the Invention

A composition comprising the following active ingredients is prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 54 g |
| b) Commercial essential oil of mint, for example mentha piperata | about 7 g |
| c) Citric acid | about 33 g |
| d) Commercially available essential oil of rosemary | about 6 g |

Carried out as described in Example 1, i.e. that the citric acid is first of all mixed with the essential oils, and then the complex of inactivated cultures is added up to complete homogenisation.

This composition can also be used as such for constituting a cosmetic or pharmaceutical composition having the same activities as those of the composition of Example 1.

The effects described in Example 1 were effectively observed:

a) On wrinkles and small wrinkles b) Tissue loosening c) Crumpled appearance due to drying out
d) the shadows under the eyes
e) the pouches
f) the treatment of scars
g) Repair of burnt tissues
h) Removal of pigment marks or skin redness
i) Promotion of the growth or the re-growth of the integuments comprising nails, hair or hairs.

A very significant improvement is also observed in the effects obtained for each one of the activities with respect to the effects obtained with the composition of Example 1. This improvement seems to be due to a combination of essential oil of mint and essential oil of rosemary as well as to the proportion of citric acid.

EXAMPLE 4
Composition According to the Invention

A composition comprising the following active ingredients can be prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 54 g |
| b) Commercial essential oil of mint, for example mentha piperata | about 5 g |
| c) Citric acid | about 30 g |
| d) Commercially available essential oil of rosemary | about 5 g |
| e) Commercially available soluble collagen | about 6 g |

Carried out as in Example 1, i.e. that the citric acid is first of all mixed with the essential oils, and then the complex of inactivated cultures is added up to complete homogenisation.

This composition can also be used as such for constituting a cosmetic or pharmaceutical composition having the same activities as those of the composition of Example 1.

EXAMPLE 5
Composition According to the Invention

A composition comprising the following active ingredients can be prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 50 g |
| b) Essential oil of mint | about 5 g |
| c) Citric acid | about 30 g |
| d) Structural proteins, in particular soluble collagen | about 15 g |

Carried out as in Example 1 for the preparation of this composition, i.e. the citric acid is first of all mixed with the essential oil, then the proteins, soluble collagen here, and then finally the complex of inactivated cultures up to complete homogeneity.

This composition can also be used as such for constituting a cosmetic or pharmaceutical composition having the activities described.

This composition is applied in order to test each one of the activities in an identical way as Examples 1 and 2. A very good effectiveness for each one of the activities is noted.

EXAMPLE 6
Composition According to the Invention

A composition having the following active ingredients is prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 50 g |
| b) Essential oil of mint | about 5 g |
| c) Citric acid | about 30 g |
| d) Hydrolysate of structural proteins, in particular collagen hydrolysate | about 10 g |
| e) Proteins hydrolysate constituted by an elastin hydrolysate | about 5 g |

Carried out as described in the preceding Example simply by further adding elastin hydrolysate. This composition can also be used as such for constituting a cosmetic or pharmaceutical composition having the activities described.

EXAMPLE 7
Composition According to the Invention

A composition having the following active ingredients is prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 50 g |
| b) Essential oil of mint | about 5 g |
| c) Citric acid | about 30 g |
| d) Structural proteins hydrolysate, in particular collagen hydrolysate | about 5 g |
| e) Proteins hydrolysate constituted by an elastin hydrolysate | about 5 g |
| f) Substance having thickening effect, for example poly(vinyl alcohol) | about 5 g |

Carried out as described in Example 1 to prepare this composition, i.e. by firstly mixing the citric acid with the essential oil or essential oils, amongst the other ingredients, except the thickening agent, and then the complex of inactivated cultures, and finally the thickening agent.

After obtaining complete homogeneity, this composition can be used as such as a cosmetic or pharmaceutical composition, and then it will be noted that the presence of thickening agents enables obtaining a chemical effect of erasing, as well as a mechanical effect which promotes the microcirculation in the capillaries which are close to the surface of the skin.

EXAMPLE 8 ACCORDING TO THE INVENTION
Composition Particularly Adapted for the Repair of Burnt Tissues This composition has the following ingredients, in percentages by weight:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 77 g |
| b) Mixture of essential oils of mint and rosemary (50/50 by weight) | 3% |
| c) Citric acid | 3% |
| d) Soluble collagen | 7% |
| e) Elastin | 7% |
| f) Texture agent | 3% |

The mixture is made in the order indicated in the preceding Examples, the texture agent being added last.

This composition is particularly adapted for treating tissues burnt by rubbing or by an intense heat. A visual improvement of these tissues is observed as from the first application and after several applications, the appearance of a skin having a surface which is essentially similar to the neighbouring zones of the skin which have not been subjected to burns.

EXAMPLE 9 ACCORDING TO THE INVENTION

An actually preferred composition according to the invention, comprising the following active ingredients, is prepared:

| | |
|---|---|
| a) Complexes of inactivated cultures of bacteria of the genus Bifidobacterium or of bacteria related to this genus at 30% available on the market and marketed by the German company Biodroga Cosmetic GmbH under the name of Biorepair ® | about 57 g |
| b) Mixture of essential oils of mint and of rosemary (50/50 by weight) | 7% |
| c) Citric acid | about 27% |
| d) Soluble collagen | about 9% |

The mixture is made as described in Example 1.

The best results for the whole of the activities indicated above in the preceding Examples are obtained with such a composition.

A protocol of application of this currently preferred composition which can also be used for applying the other compositions according to the invention is the following:
a) optionally carrying out an erasure as is well-known to the beautician,
b) application of the composition only on the parts to be treated,
c) carrying out an erasure on these same parts, above all in the case of the treatment of the zones of skin wrinkled for carrying out mechanical work.

In a variant of this protocol, before the application of the composition according to the invention, an application of a moisturising product can be made on the whole of the face, and then penetrating this mixture with the aid of a serum which penetrates very rapidly and takes with it the active ingredients of the composition according to the invention. This serum, can have the composition indicated above in the present description.

EXAMPLE 10 ACCORDING TO THE INVENTION

Cosmetic Composition for Nails

A composition having the following active ingredients, in percentage by weight, is prepared:
1°. Component A: about 70%

| | |
|---|---|
| a) Complexes of inactivated cultures of bacteria of the genus bifidobacterium or of bacteria related to this genus at 30% available on the market and marketed by the German company Biodroga Cosmetic GmbH under the name of Biorepair ® | about 57% |
| b) Citric acid | about 27% |
| c) Essential oil of mint alone or mixed with an essential oil of rosemary (50/50 by weight) | about 7% |
| d) Soluble collagen | about 9% |

2°. Component B: about 30%
Discoloured tincture of iodine

Carried out as in Example 1 for the preparation of this composition, i.e. the citric acid is firstly mixed with the essential oil, and then soluble collagen and then finally the complex of inactivated culture up to complete homogeneity, and then the component B is added into the component A thus formed.

A positive effect on the growth of the integuments is noted when this composition is applied onto the nails.

EXAMPLE 11 ACCORDING TO THE INVENTION

Cosmetic Composition for the Hair

The following composition is prepared:
1°. Component A

Complexes of inactivated cultures of bacteria of the genus Bifidobacterium or of bacteria related to this genus at 30% available on the market and marketed by the German company Biodroga Cosmetic GmbH under the name of Biorepair® 100%.

2°. Compound B: about 30%
Minoxydil

Carried out as described in the preceding Example, by firstly mixing the whole of the active ingredients of component A as indicated in this Example 10, and the component B is then added into component A.

A quantifiable difference is observed as from the second month of application when this composition is applied every day. Firstly, small hairs are observed which re-grow a little everywhere in the area of baldness and then the patches wherein the re-growth gets denser.

COMPARATIVE EXAMPLE 12

The following composition is prepared:

Complexes of inactivated cultures of bacteria of the genus Bifidobacterium or of bacteria related to this genus at 30% available on the market and marketed by the German company Biodroga Cosmetic GmbH under the name of Biorepair® . . . 100%.

This composition applied topically onto the skin, even for a week, gives no significant anti-wrinkles effect, nor any apparent effect on the appearance of old scars. No effect is also noted as regards skin healing, removing pigment marks and for promoting the growth or re-growth of the integuments.

COMPARATIVE EXAMPLE 13

The following composition is prepared:

Commercially available oil of mint, mentha piperata . . . 100%

This composition is applied topically onto the skin for one week, and no detectable anti-wrinkles or old scars effect is noted. Similarly, no effect of repair is noted of burnt tissues, of healing, no effect on pigment marks nor any effect of promotion of growth or re-growth of the integuments is noted.

In contrast, essential oil of mint causes mild surface burns.

EXAMPLE 14 OF THE INVENTION

The following cosmetic or pharmaceutical composition is prepared:

| | |
|---|---|
| a) Fermented sunflower flower pollen having a concentration of living or inactivated micro-organisms of about 10 million per gram This pollen is constituted by fresh pollen originating from the hive mixed with an aqueous solution enriched with lactic flora of the genus bifidus or lactobacillus or streptococcus at a content of greater than 10 million micro-organisms per | about 4.5%. |

-continued

| | |
|---|---|
| gram of broth, broth representing 30% by weight of the pollen and after mixing the pollen with the broth, it is left to ferment or soak at ambient temperature for 1 day. The fermented pollen is then collected by a classical technique of centrifugation-filtration which leads to a concentration which enables a concentration of living or inactivated micro-organisms preferably of greater than about at least 10 million micro-organisms per gram of concentrated products. | |
| b) Essential oil of mint | about 5% |
| c) Citric acid | about 7% |
| d) Sunflower vegetable oil | about 20% |
| e) Thickening agent, such as poly(vinyl alcohol) or polyvinylpyrrolidone | 10% |
| f) Triethanolamine to bring the pH to about 5.5 | about 1% |
| g) Gellifying agent such as carbopol | about 0.4% |
| h) Perfumed water of cosmetic or pharmaceutical quality QSP | 100% |

In order to prepare this composition, citric acid is first or all mixed with the essential oil, and then the other ingredients, except the gellifying agent and the thickening agent, and then the fermented pollen, with one part only of water, the remaining part of water serving to mix the carbopol in order to prepare a pre-gel which will then be added to the solution prepared with the other ingredients after having added the gellifying agent thereto, so as to finally constitute a gel, as is well known in the art.

After a homogenous gel is obtained, this composition can be used as it is, as a cosmetic or pharmaceutical composition.

An application of this composition topically on the skin, for 1 week, enables obtaining an anti-wrinkles, smoothening, skin texture improving, lightening, scar healing, skin surface moisturising, skin softening, perfuming, skin regenerating effect, as set forth above.

EXAMPLE 15 OF THE INVENTION

| Cosmetic or pharmaceutical composition | |
|---|---|
| a) Fermented pollen as used in Example 14 | about 5% |
| b) Essential oil of lemon or of orange | about 3% |
| c) Citrus fruit juice, such as lemon juice | about 30% |
| d) First cold pressed soya vegetable oil | about 10% |
| e) Substances having a thickening effect, for example pectin or agar | about 10% |
| f) Triethanolamine to bring the pH to about 5.5 | about 1%. |
| g) Perfumed water of cosmetic or pharmaceutical quality QSP | 100%. |

In order to prepare this composition, the citrus fruit juice, such as lemon juice, is firstly mixed with the essential oil, and then the other ingredients, except the thickening agent, and then the fermented pollen, and finally the thickening agent.

After complete homogeneity has been obtained, this composition can be used as it is, as a cosmetic or pharmaceutical composition with the same effects as those described in the preceding example, but in a more reinforced way.

What is claimed is:

1. A topical cosmetic care or pharmaceutical treatment composition which comprises, by weight, 1 to 90% of an inactive culture of bacteria of the genus Bifidobacterium compatible in cosmetics or pharmacy, in a mixture with 0.5 to 10% of at least one essential oil, and 1 to 50% of an organic acid.

2. The composition of claim 1, wherein said organic acid is a fatty acid.

3. The composition of claim 1, wherein said organic acid is selected from the group consisting of citric acid, a citric acid compound, tartaric acid, ascorbic acid, lactic acid, a citrus fruit juice containing at least one said organic acid, and a fatty acid compatible in cosmetics or pharmacy.

4. The composition of claim 3, wherein said citric acid compound is a citric acid salt or a citric acid ester.

5. The composition of claim 4, wherein said citric acid ester is a citric acid alcoholic ester.

6. The composition of claim 3, wherein said citrus fruit juice is selected from the group consisting of lemon juice, orange juice, lime juice, grapefruit juice, clementine juice and mandarin juice.

7. The composition of claim 1, wherein said essential oil is an essential oil of a citrus fruit selected from the group consisting of an essential oil of lemon, and an essential oil of orange.

8. The composition of claim 1, wherein said acid is selected from the group consisting of citric acid, tartaric acid, ascorbic acid and lactic acid.

9. The composition of claim 1, wherein said essential oil is at least one plant essential oil selected from the group consisting of an essential oil of mint, an essential oil of rosemary, an essential oil of thyme, an essential oil of wild thyme and mixtures thereof.

10. The composition of claim 1, further comprising a protein.

11. The composition of claim 10, wherein said protein is a structural protein selected from the group consisting of collagen and elastin.

12. The composition of claim 11, wherein said structural protein is in a soluble form or is a hydrolysate thereof.

13. The composition of claim 1, wherein the concentration of the inactive Bifidobacterium culture is at least 1 million micro-organisms per gram of culture.

14. The composition of claim 1, wherein the concentration of the inactive Bifidobacterium culture is at least 10 million micro-organisms per gram of culture.

15. The composition of claim 1, which comprises 0.5 to 10% by weight of essential oil of mint.

16. The composition of claim 1, which comprises 1 to 7% by weight of essential oil of mint.

17. The composition of claim 1, which comprises 0.5 to 10% by weight of an essential oil other than essential oil of mint.

18. The composition of claim 17, which comprises 1 to 7% by weight of an essential oil other than essential oil of mint.

19. The composition of claim 17, wherein said essential oil other than essential oil of mint is selected from the group consisting of an essential oil of rosemary, an essential oil of thyme and an essential oil of wild thyme.

20. The composition of claim 1, wherein the essential oil is present in a total amount not greater than 10% by weight.

21. The composition of claim 1, which comprises 5 to 40% by weight of said acid.

22. The composition of claim 21, which comprises 5 and 30% by weight of said acid.

23. The composition of claim 1, wherein the mixture N comprises a maximum of 30% by weight of the composition, with a remaining portion comprising cosmetically or pharmaceutically acceptable excipients.

24. The composition of claim 23, wherein said excipients are cosmetically acceptable.

25. The composition of claim 1, wherein said at least one essential oil a plant essential oil selected from the group consisting of an essential oil of mint, of an essential oil of rosemary, an essential oil of thyme, an essential oil of wild thyme, and any one of a mixture thereof.

26. A cosmetic or pharmaceutical composition, which comprises from 1 to 90% by weight of an inactivated culture of bacteria of the genus Bifidobacterium, in admixture with from 5 to 30% by weight of an organic acid and from 1 to 7% by weight of at least one essential oil.

27. The composition of claim 26, wherein said at least one essential oil is a plant essential oil selected from the group consisting of an essential oil of mint, of an essential oil of rosemary, an essential oil of thyme, an essential oil of wild thyme, and mixtures thereof; and said organic acid is selected from the group consisting of citric acid, a citric acid salt, a citric acid ester, a citric alcoholic ester, tartaric acid, ascorbic acid, lactic acid, a citrus fruit juice containing at least one said organic acid, and a fatty acid compatible in cosmetics or pharmacy.

28. A cosmetic or pharmaceutical composition, which comprises, as active ingredients, in percentage by weight:
    a) about 57% of an activated culture of bacteria of the genus Bifidobacterium,
    b) about 27% of citric acid,
    c) about 7% of essential oil of mint, and
    d) about 9% of soluble collagen.

29. A cosmetic or pharmaceutical composition, which comprises, as active ingredients, in percentage by weight:
    a) about 57% of an inactivated culture of bacteria of the genus Bifidobacterium at 30%,
    b) about 27% of citric acid,
    c) about 7% of essential oil of mint alone, and
    d) about 9% of soluble collagen.

30. A cosmetic or pharmaceutical composition, which comprises, as active ingredients, in percentage by weight:
    a) about 57% of an inactivated culture of bacteria of the genus Bifidobacterium,
    b) about 27% of citric acid,
    c) about 7% of essential oil of mint mixed with an essential oil of rosemary (50/50 by weight), and
    d) about 9% of soluble collagen.

31. A cosmetic or pharmaceutical composition, which comprises, as active ingredients, in percentage by weight:
    about 70% by weight of a first component containing
    a) about 57% of an inactivated culture of bacteria of the genus Bifidobacterium at 30%,
    b) about 27% of citric acid,
    c) about 7% of essential oil of mint mixed with an essential oil of rosemary (50/50 by weight),
    d) about 9% of soluble collagen; and
    about 30% by weight of a second component which is discolored tincture of iodine.

32. A method of treatment of a mammal, selected from the group consisting of a cosmetic care and a pharmaceutical treatment, said treatment or care being selected from the group consisting of an anti-wrinkle method, a skin regenerating method, an anti-wrinkle method, old scar erasing method, a method for repairing scars left by burns, a method for promoting skin healing, a method for removing pigment marks, a method permitting a lightening of the skin, skin surface moisturizing, and skin softening, comprising the topical delivery to said mammal of a composition comprising, by weight, 1 to 90% of an inactivated culture of bacteria of the genus Bifidobacterium in a mixture with 0.5 to 10% of at least one essential oil, and 1 to 50% of an organic acid, in an amount effective to perform said treatment.

33. The method of claim 32, wherein said mammal is a human being or an animal.

34. The method of claim 32, wherein the inactive Bifidobacterium culture is cosmetically acceptable.

35. The method of claim 32, wherein the inactive Bifidobacterium culture is pharmaceutically acceptable.

36. The method of claim 32, wherein said organic acid is a fatty acid.

37. The method of claim 32, additionally comprising topically applying a moisturising agent prior to topical application of said mixture.

38. The method of claim 37, wherein said moisturising agent is a serum.

39. The method of claim 32, wherein the inactive Bifidobacterium culture is used at a concentration of at least 1 million microorganisms per gram of culture.

40. The method of claim 32, wherein the inactive Bifidobacterium culture is used at a concentration of at least 10 million microorganisms per gram of culture.

41. A method of cosmetic care selected from the group consisting of an anti-wrinkle method, a skin regenerating method, an anti-wrinkle activity, old scar erasing method, a method for repairing scars left by burns, a method for promoting skin healing, a method for removing pigment marks, a method permitting a lightening of the skin, skin surface moisturizing, and skin softening, comprising topical application to said skin areas in need thereof of a cosmetically effective amount to perform said cosmetic care of a composition comprising, by weight, 1 to 90% of an inactivated culture of bacteria of the genus Bifidobacterium, in a mixture with 0.5 to 10% of at least one essential oil, and 1 to 50% of an organic acid.

* * * * *